United States Patent
Sugawara et al.

(10) Patent No.: US 9,646,649 B2
(45) Date of Patent: May 9, 2017

(54) MEDICAL IMAGE DATA INFORMATION EXCHANGE SYSTEM

(71) Applicant: HEART ORGANIZATION CO., LTD., Osaka (JP)

(72) Inventors: Toshiko Sugawara, Osaka (JP); Yuichi Oishi, Osaka (JP)

(73) Assignee: HEART ORGANIZATION CO., LTD., Osaka (JP)

( * ) Notice: Subject to any disclaimer, the term of this patent is extended or adjusted under 35 U.S.C. 154(b) by 20 days.

(21) Appl. No.: 14/785,407

(22) PCT Filed: Jan. 31, 2014

(86) PCT No.: PCT/JP2014/000514
§ 371 (c)(1),
(2) Date: Oct. 19, 2015

(87) PCT Pub. No.: WO2014/174739
PCT Pub. Date: Oct. 30, 2014

(65) Prior Publication Data
US 2016/0071547 A1 Mar. 10, 2016

(30) Foreign Application Priority Data

Apr. 22, 2013 (JP) .................................. 2013-089257

(51) Int. Cl.
*H04N 5/93* (2006.01)
*H04N 9/80* (2006.01)
(Continued)

(52) U.S. Cl.
CPC ............ *G11B 27/036* (2013.01); *A61B 5/742* (2013.01); *A61B 6/463* (2013.01); *A61B 6/468* (2013.01);
(Continued)

(58) Field of Classification Search
CPC .... G11B 27/036; G11B 27/3081; H04N 5/76; A61B 19/5212; A61B 5/742; G06F 19/321
(Continued)

(56) References Cited

U.S. PATENT DOCUMENTS

2005/0180728 A1* 8/2005 Ichioka ................ G11B 27/005
386/261
2006/0271403 A1 11/2006 Iwasa et al.
(Continued)

FOREIGN PATENT DOCUMENTS

CN 1873676 A 12/2006
JP 2005-278991 A 10/2005
(Continued)

OTHER PUBLICATIONS

European Search Report for Corresponding European Application No. 14787794.8, mailed Aug. 24, 2016.
(Continued)

*Primary Examiner* — Robert Chevalier
(74) *Attorney, Agent, or Firm* — Jason H. Vick; Sheridan Ross, PC

(57) ABSTRACT

[Problem] To efficiently and effectively exchange information on medical image data. [Solution] A video image extracted from a DICOM file is uploaded from an upload terminal (6) to a server (2). A medical personnel accesses medical image data from a viewing terminal (8a) and plays the video image provided by the server. The user inputs a comment, into which link destination information to the medical image data is incorporated (inserted), via a comment input field on a medical image viewing screen.

16 Claims, 23 Drawing Sheets

(51) Int. Cl.

| | | |
|---|---|---|
| *G11B 27/036* | (2006.01) | |
| *G06Q 50/24* | (2012.01) | |
| *A61B 6/00* | (2006.01) | |
| *G06F 19/00* | (2011.01) | |
| *G11B 27/30* | (2006.01) | |
| *H04N 5/76* | (2006.01) | |
| *A61B 90/00* | (2016.01) | |
| *A61B 5/00* | (2006.01) | |
| *A61B 6/03* | (2006.01) | |
| *A61B 5/055* | (2006.01) | |

(52) U.S. Cl.
CPC .............. *A61B 6/487* (2013.01); *A61B 6/563* (2013.01); *A61B 90/361* (2016.02); *G06F 19/321* (2013.01); *G06Q 50/24* (2013.01); *G11B 27/3081* (2013.01); *H04N 5/76* (2013.01); *A61B 5/0022* (2013.01); *A61B 5/055* (2013.01); *A61B 5/743* (2013.01); *A61B 6/03* (2013.01); *A61B 6/467* (2013.01)

(58) Field of Classification Search
USPC ........ 386/241, 239, 240, 248, 278, 281, 290
See application file for complete search history.

(56) References Cited

U.S. PATENT DOCUMENTS

| | | |
|---|---|---|
| 2007/0066875 A1 | 3/2007 | Horn et al. |
| 2007/0258638 A1 | 11/2007 | Howerton, Jr. |

FOREIGN PATENT DOCUMENTS

| | | |
|---|---|---|
| JP | 2007-012044 A | 1/2007 |
| JP | 2009-080545 A | 4/2009 |
| JP | 2009-142388 A | 7/2009 |
| JP | 2011-019926 A | 2/2011 |
| JP | 2012-230528 A | 2/2011 |
| JP | 2012-230528 A | 11/2012 |

OTHER PUBLICATIONS

International Preliminary Report on Patentability (including translation) for corresponding International Application No. PCT/JP2014/000514, mailed Nov. 5, 2015.

International Search Report for corresponding International Application No. PCT/JP2014/000514, mailed Mar. 25, 2014.

Notification of Reasons for Refusal (including translation) for corresponding Japanese Application No. 2013-089257, mailed Feb. 13, 2017.

* cited by examiner

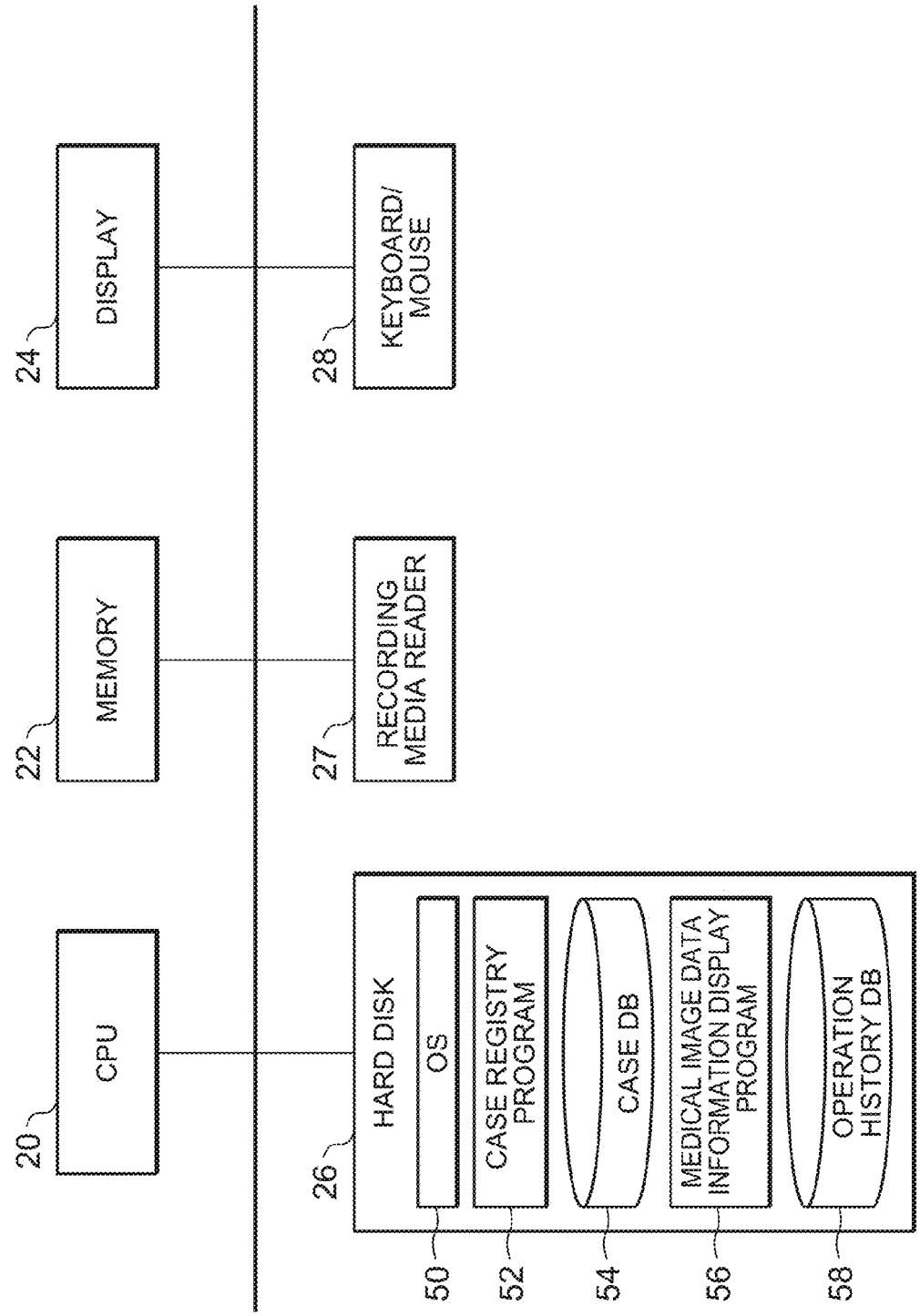

FIG.6

Please log in !

ID

[                    ]

Password

[                    ]

☐ Forgot password ?

[ Log In ! ]

FIG.8

The 14th seminar of Angioplasty of Chronic Total Occlusions
CTO Club Meeting May 9-10, 2013 operator

Point of the case

● clinical background

Age   SELECTING IN PULL-DOWN MANNER
(OPTION: under 30s, 31-35, 36-40, 41-45, 70, 71-75, 76-80, over 80s)

Sex   SELECTING IN PULL-DOWN MANNER
(OPTION: F/M)

Key Word  SELECTING IN
          PULL-DOWN MANNER

-Coronary
    -CTO
    -LMT
    -Bifurcation
    -Long lesion
    -Ostial
    -In-stent Resetenosis
    -Other lesion subset
-Imaging
-Endovascular
-Structural Heart Diseases
-Adjunctive Pharmacorogy Risk Factor/Complication   FREE DESCRIPTION ● Procedure
FREE DESCRIPTION

REGISTRATION

COMMENT HISTORY TABLE (CASE ID: Case 1)

| INPUT TIME | CONTENT OF COMMENT | USER NAME |
|---|---|---|
| ○○ : × × : □□ | I · · · THAT × × BY ○○ | USER A |
| ○○ : × × : △△ | I SEE. · · · | USER B |

MEDICAL IMAGE DATA INFORMATION EXCHANGE SYSTEM

CROSS REFERENCE TO RELATED APPLICATIONS

This application is a national stage application under 35 U.S.C. 371 of PCT Application No. PCT/JP2014/000514 having an international filing date of 31 Jan. 2014, which designated the United States, which PCT application claimed the benefit of Japanese Application No. 2013-089257 filed 22 Apr. 2013, each of which are incorporated herein by reference in their entirety.

TECHNICAL FIELD

The present invention relates to a technique for exchanging information on medical image data.

BACKGROUND ART

A PACS (Picture Archiving and Communication System) is a term used to describe a set of medical image systems that store and manage digital medical image data from CR, CT, MRI and the like used in clinical practice, and use an online network to communicate and transfer the digital medical image data. In general, the PACS refers to a set of systems that includes not only a medical image server and viewer, but also a reporting system, a Radiology Information System (RIS) and the like.

The DICOM (Digital Imaging and Communications in Medicine) standard serves as the standard for the PACS system. The DICOM standard is a global standard for medical image taken with MRI, CT or the like, and defines mainly a data format and a communication specification of medical image information.

Following the DICOM standard, not only images taken with MRI or CT, but also data related to medical practice such as motion video data, sound data and the like created from endoscopes, ultrasounds or the like, can be unified and managed. More specifically, any image data taken with a different type of digital image device in a different hospital can be shared through a network and a recording media.

Currently, there are various techniques utilizing a DICOM file (files created conforming to the DICOM standard) (JP-A-2005-278991 and JP-A-2009-142388).

JP-A-2005-278991 discloses a system in which medical image data included in a DICOM file is used for a telediagnosis.

JP-A-2009-142388 discloses that a specific frame image included in the DICOM file is stored in association with a time-series order information in order to reduce the operation burden when the image is read out from the second time onward. This makes it possible to, for example, play a motion video image from any desired point based on the specific frame image having order information set by a user.

SUMMARY OF THE INVENTION

Problem to be Solved by the Invention

However, according to a technique described in Patent Literature 1, it is possible to only exchange a comment on medical image data being viewed, and it is thus difficult to make a comparison with or reference to other medical image data. In addition, there has been a problem that medical image data in a DICOM file includes personal information such as the name of the patient, and therefore is not suitable to be shared unaltered with a plurality of people.

With the technique described in Patent Literature 2, a key image for determination of order information must be selected by a user, and therefore, the operation has been cumbersome.

The purpose of the invention is to provide a system that enables the exchange of comments by simply linking to motion video data.

Means for Solving the Problem (1)(2)(3)(4)(5) An image data providing system according to the invention is characterized in that:

a server device includes;

a recording part that records each frame of motion video image data as a still image and a consecutive number of playing order as a motion video as a file name or an index name of each of the still images and records a comment input from a terminal device, first transmission means that receives a playing instruction from the terminal device and transmits the still images, and second transmission means that receives a link destination acquisition instruction from the terminal device and acquires the still image corresponding to the consecutive number described in the file name or the index name included in the link destination acquisition instruction, and then transmits the still image, wherein the terminal device includes first display control means that displays a series of the still images transmitted from the server device in response to the playing instruction as a motion video by playing in consecutive numerical order described in the file name or the index name and, also displays the comment, and link destination acquisition instruction transmission means that transmits the link destination acquisition instruction with the consecutive number to the server device when a link displayed in the comment is selected based on link information including the consecutive number, and second display control means that displays the still images transmitted from the server device in response to the link destination acquisition instruction.

Thus, it is possible to link to an image that constitutes a part of the motion video recorded in the server directly and simply.

(6)(7)(8)(9)(10) An image data providing system according to the invention is characterized in that:

a server device includes a recording part that records a motion video image data and a comment, first transmission means that receives a playing instruction from a terminal device and transmits the motion video data, and second transmission means that receives a link destination acquisition instruction from the terminal device and acquires a frame image corresponding to a frame number included in the link destination acquisition instruction, and then transmits the frame image, wherein the terminal device includes first display control means that displays the motion video data and the comment transmitted from the server device in response to a playing instruction, link destination acquisition instruction transmission means that transmits the link destination acquisition instruction with the frame number to the server device when a link displayed in the comment is selected based on the link information including the frame number, and second display control means that displays the frame image transmitted from the server device in response to the link destination acquisition instruction.

Thus, it is possible to create a link without, for example, indexing to the motion video.

(11) An image data providing system according to the invention is characterized in that, a terminal device includes a link information insertion means which, when a link operation is made by a user when displaying the motion video by the first display control mechanism, creates the link information specifying a frame number of displayed motion video and inserts it in the comment.

Thus, the link to the image can be inserted in the comment by simple operations.

(12) An image data providing system according to the invention is characterized in that, a terminal device that includes a link information insertion means in which a link operation is made by a user when displaying the motion video by the first display control means, and then the link information specifying the consecutive number of displayed motion video is created and inserted in the comments.

Thus, the link to the image can be inserted in the comment by simple operation.

(13) An image data providing system according to the invention is characterized in that, a server device includes means for storing a user's operation history of a terminal device when playing a motion video, and means for determining a display method of playing the motion video from a next time onward based on the user's operation history.

Thus, the display form when playing can be varied based on the user's viewing history.

(14) An image data providing system according to the invention is characterized in that, an operation history which is the number of pause operations stored with respect to each frame of the image data.

Thus, the display form when playing can be varied depending on the number of pause operation by each user.

(15) An image data providing system according to the invention is characterized in that, an operation history displays frequency with respect to each frame.

Thus, the display form when playing can be varied depending on the number of times that the motion video was played by each user.

(16) An image data providing system according to the invention is characterized in that, the first transmission means of the server device transmits information of a frame to be thumbnailed with the comment and the motion video data, wherein the frame to be thumbnailed is determined based on the operation history.

Thus, an image believed to be important can be selected and thumbnailed.

(17)(18) A medical image data providing system according to the invention is characterized by including means for extracting a plurality of medical image data from contents data including a motion video image data, means for storing the user's operation history when playing the motion video image, and means for determining a display method when the motion video image is viewed from a next time onward based on the content of the user's operation history.

Thus, the display method of the motion video can be determined depending on the user's operation history.

BRIEF DESCRIPTION OF THE DRAWINGS

FIG. 2 is a diagram illustrating the hardware configuration of medical image data providing system 2;

FIG. 6 is a diagram illustrating a display example of a login screen;

FIG. 8 is a diagram illustrating a display example of an attribute information entry screen when uploading;

FIG. 11 is a diagram illustrating a data example of a comment history table;

EMBODIMENTS OF THE INVENTION

1. System Summary

Figure 1A:
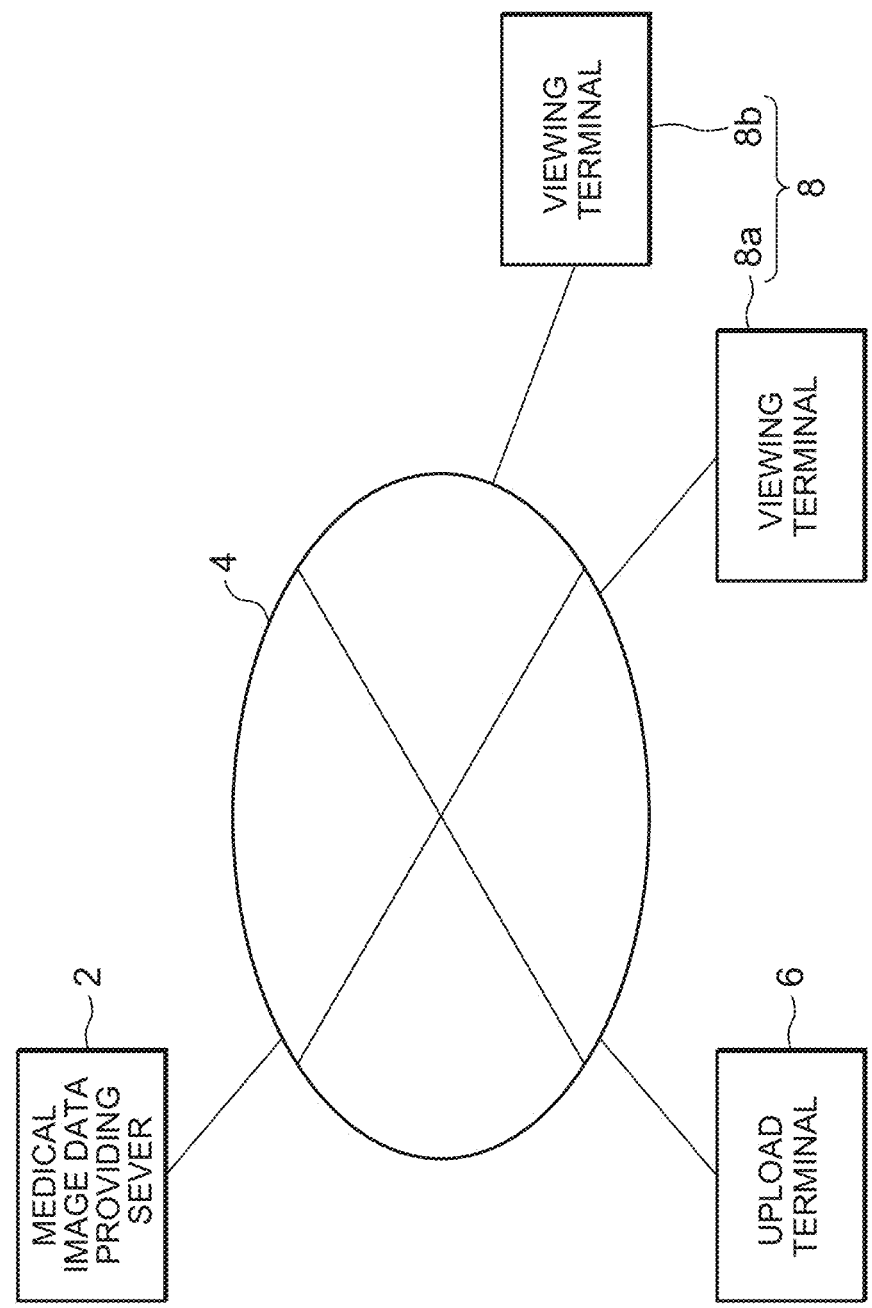
FIG. 1A is a diagram illustrating the configuration of a medical image data providing system according to the present invention.

As shown in the FIG. 1A, a medical image data information exchange system according to the present invention includes a medical image data providing system (server) 2 containing a database in which the motion video image is registered, and an upload terminal 6 and a viewing terminal 8 (8a, 8b) connected to the server 2 via a network 4. In the following embodiment, an example that contents data is in a DICOM file form will be described.

A motion video image (a plurality of medical image data) extracted from the DICOM file is uploaded to the server 2 from the upload terminal 6. The DICOM file is contents data including at least one or more motion video created in such a way that a doctor presses a foot button to turn on/off imaging when surgery. The motion video image includes, for example, an angiographic motion video and a continuous image taken by CT, MRI, X-ray and the like while shifting spatially.

A user (medical personnel) who wishes to view a medical image accesses a medical image in the server 2 from the viewing terminal 8a via a viewing program such as a web browser to play a motion video image provided by the server. The user also carries out an operation such as a pause operation and a frame advance operation when playing the motion video image. At the same time, the operation is stored in the database of the server 2.

The user who views the motion video image, in a comment input field of a medical image viewing screen, inputs a comment into which link destination information to a specific medical image to be compared and referred to is incorporated in association with the medical image. Thus, the user can access the medical image in the link destination immediately just by clicking a link part in the input comment.

Furthermore, a display method (such as highlighting of a frame in which a pause operation was carried out many times) when the motion video image is viewed from next time onward is determined for a user who carries out an operation of other viewing terminal 8b based on an operation history (including a pause operation) when playing the motion video image. Thus, a system that allows medical personnel to mutually exchange information can be established.

Figure 1B:
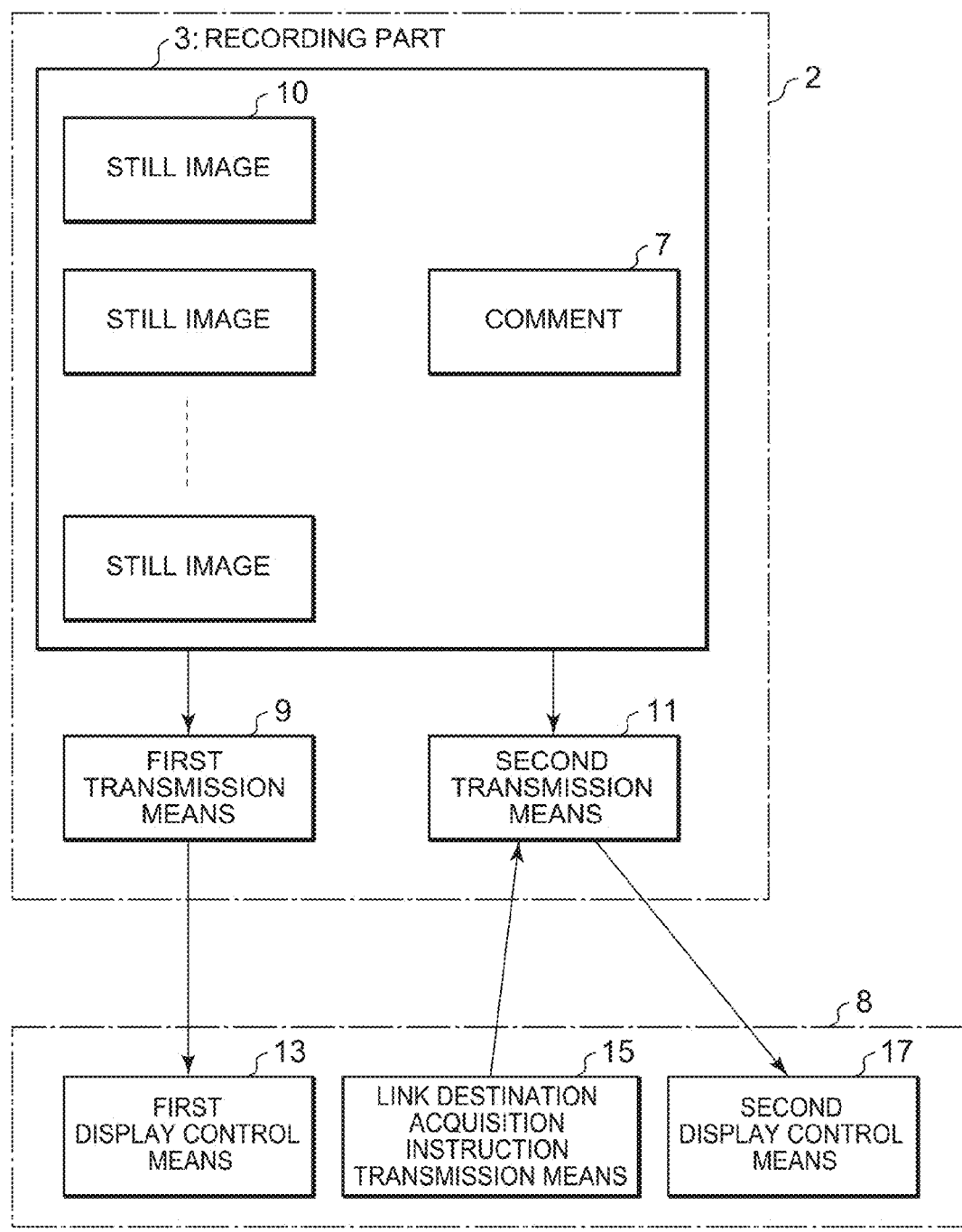
FIG. 1B is a functional block diagram of a medical image data providing system according to the present invention.

In the FIG. 1B, a functional block diagram of the system according to one embodiment of the invention is shown. A recording part 3 of the server device 2 records each frame of the motion video data as still image 5. In addition, the frame number of the frame is assigned to file names of each of the still images 5. Furthermore, the recording part 3 also records a comment 7. The comment 7 is input by the user of the terminal device 8. A series of the still images 5 and the comment 7 are read out from the recording part 3 and transmitted to the terminal device 8 by first transmission means 9.

First display control means 13 of the terminal device 8 receives the still images and the comment, and then displays them in a display part, wherein the still images are played in the order of the file names of the still images. The file names of the still images are frame numbers, resulting in playing the motion video. The comment 7 is also displayed together.

When the user of the terminal device 8 clicks a link embedded in the comment 7, a link destination acquisition instruction including link information is transmitted to the server device 2 by link destination acquisition instruction transmission means 15. A URL based on the file names of the still images 5 as link information is embedded in the comment 7.

Second transmission means 11 of the server device 2 that received the link information reads out the corresponding still image 5 from the recording part 3 and transmits it to the terminal device 8. Second display control means 17 of the terminal device 8 displays the still image 5 in the display part.

The details of the medical image data information exchange system mentioned above will be described below.

2. Hardware Configuration

In the FIG. 2, a hardware configuration of a medical image data providing server 2 (FIG. 1) is shown.

The medical image data providing server 2 is composed of a PC containing a CPU 20, a memory 22, a display 24, a hard disk 26, a recording media reader 27, and a keyboard/mouse 28, as shown in the FIG. 2.

The hard disk 26 records an OS (operating system) 50 such as WINDOWS™, a case registry program 52, a case DB 54, a medical image data information display program 56, and an operation history DB 58.

The case registry program 52 and the medical image data information display program 56 function in cooperation with the OS (operating system) 50. The OS (operating system) 50, the case registry program 52 and the medical image data information display program 56, which are recorded in the recording media, are installed on the hard disk 26 via the recording media reader 27.

In the FIG. 3, a data structure of a case DB 43 included in the medical image data providing server 2 is shown. Extraction of the image data from the DICOM file can be achieved by analyzing a data structure of the DICOM file and specifying an image at a specific position.

Figure 3A:
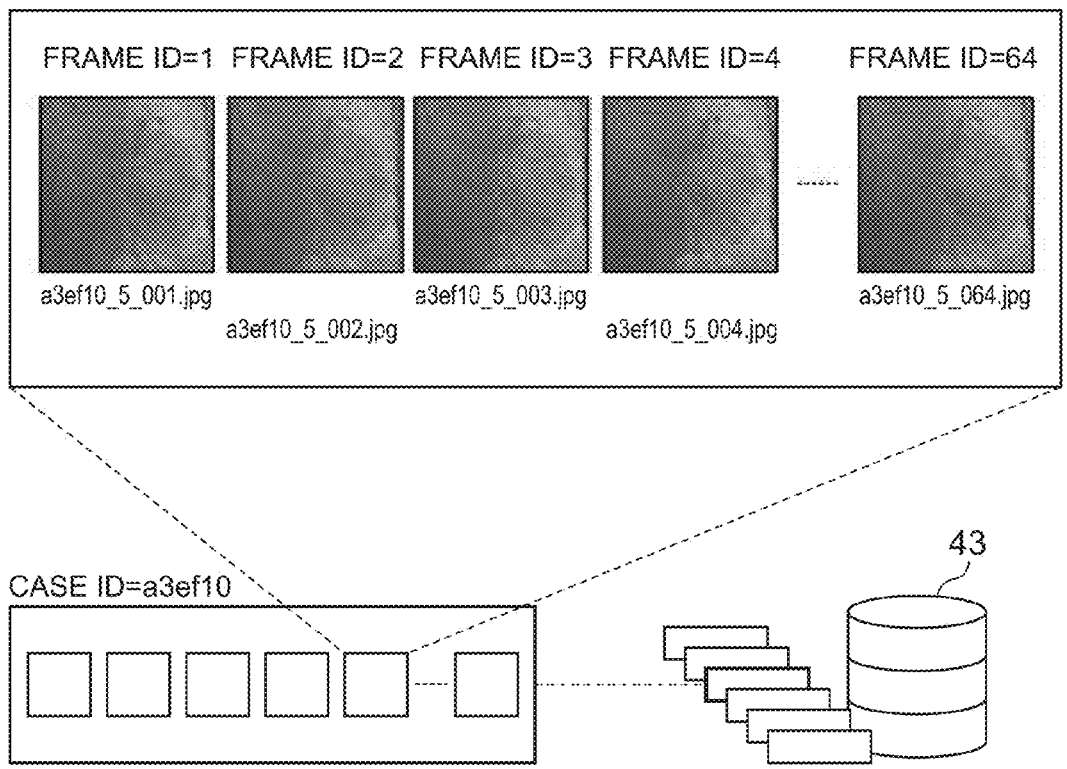
FIGS. 3A and 3B are diagrams illustrating a data example of the case DB 54.
Figure 3B:

As shown in the FIG. 3A, the case is composed of an arbitrary number of series, and each series is composed of an arbitrary number of frames. One frame corresponds to one image file and is stored on the system in a state that the file name including a string of letters "[case ID]_[series ID]_[frame ID]" is given to the frame, so that the frame can be uniquely identified in the system. As shown in the FIG. 3B, the frame may be maintained in a state that the frame can be uniquely identified by having information associating the letters with the file name in a database table. Hereinafter, "#" is used as a symbol representing the frame ID for illustrative purposes.

A user's operation history (such as a content of an operation, and number of operations) when viewing the motion video image is stored in the operation history DB 58 (FIG. 2) of the medical image data providing server 2 via the viewing terminal 8 (FIG. 1). A description of data example of the operation history DB 58 will be given later.

Figure 4:
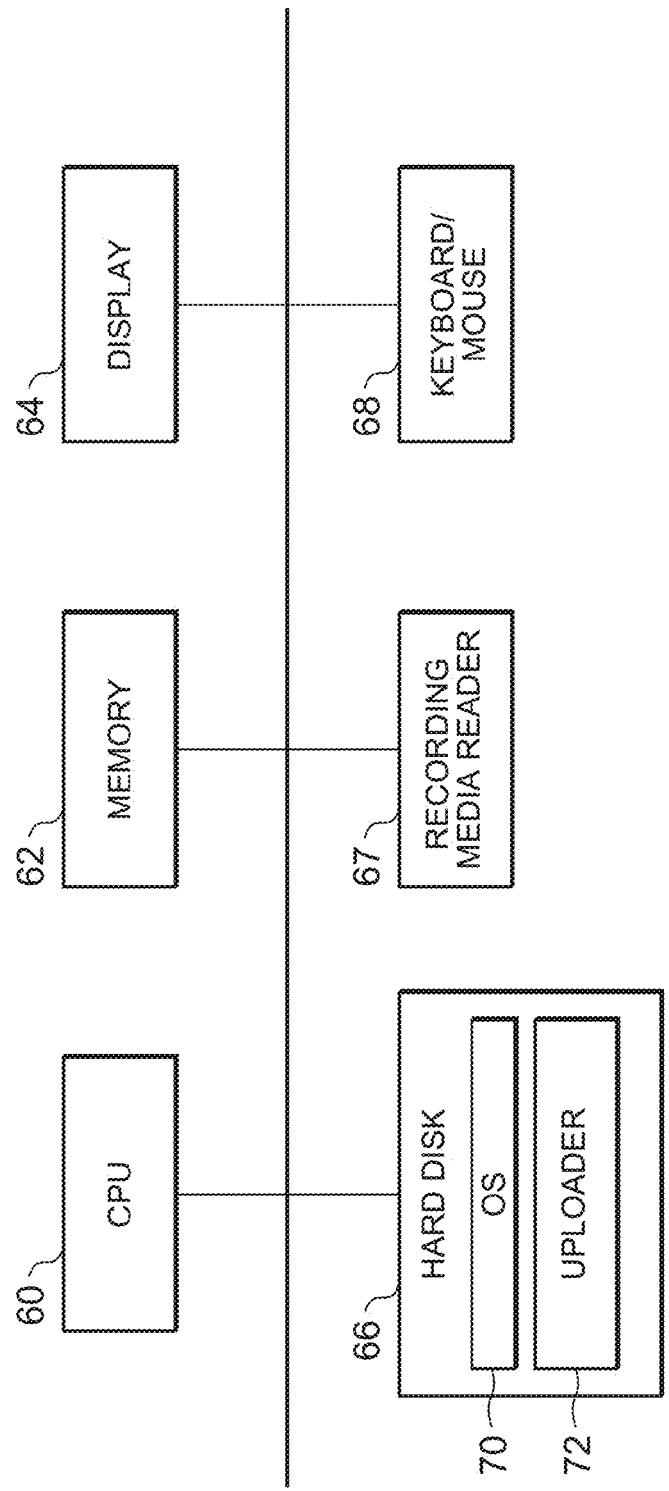
FIG. 4 is a diagram illustrating a hardware configuration of upload terminal 6.

In the FIG. 4, a hardware configuration of the upload terminal 6 (FIG. 1) is shown.

As shown in the FIG. 4, the upload terminal 6 is composed of a PC containing a CPU 60, a memory 62, a display 64, a hard disk 66, a recording media reader 67, and a keyboard/mouse 68. The hard disk 66 records an OS (operating system) 70 such as WINDOWS™, and an uploader 72 for uploading a medical image data. A user can access the medical image data providing server 2 via the uploader 72.

Figure 5:
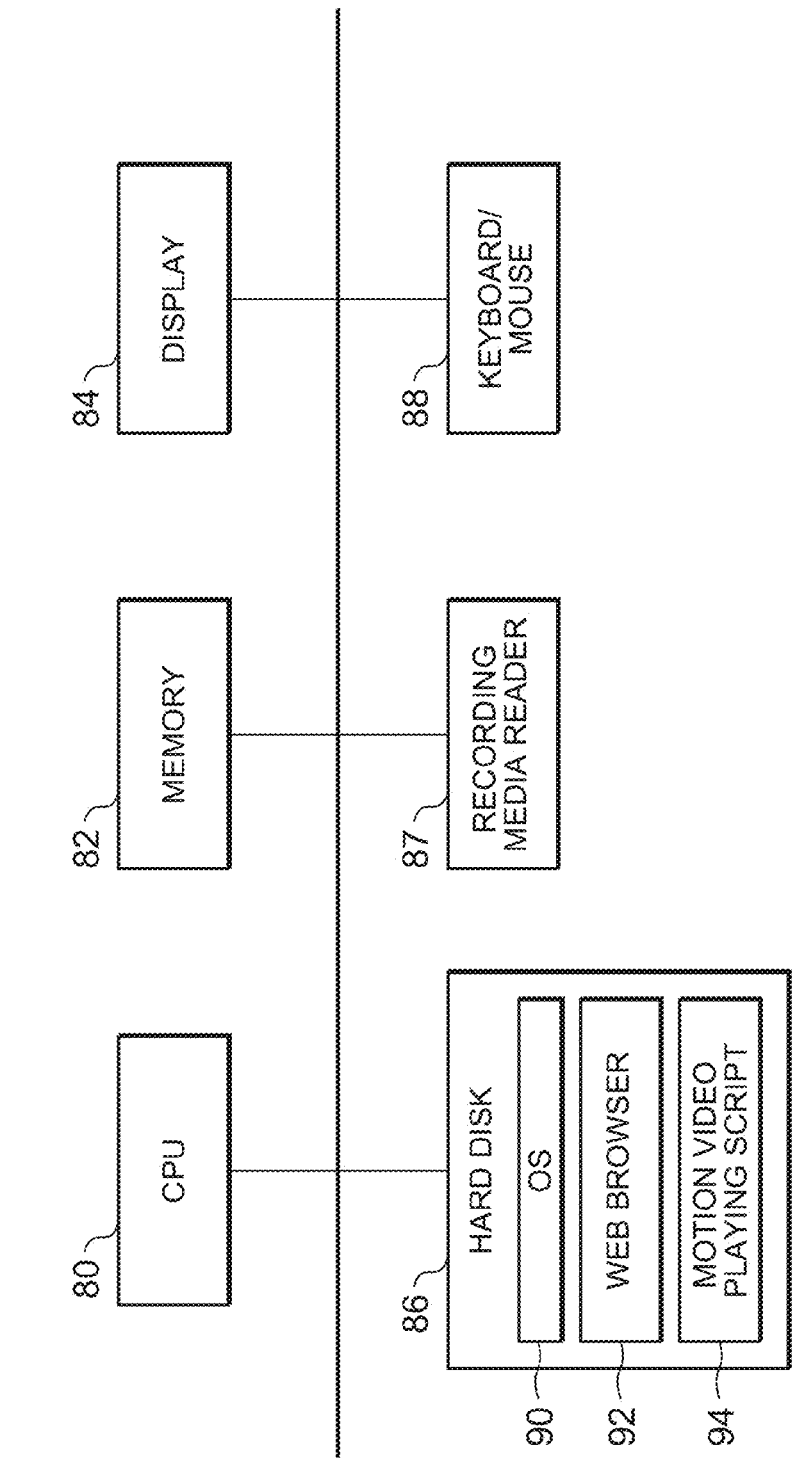
FIG. 5 is a diagram illustrating a hardware configuration of viewing terminal 8.

In the FIG. 5, a hardware configuration of the viewing terminal 8 (8a, 8b) (FIG. 1) is shown.

As shown in the FIG. 5, the viewing terminal 8 is composed of a PC containing a CPU 80, a memory 82, a display 84, a hard disk 86, a recording media reader 87, and a keyboard/mouse 88. The hard disk 86 records an OS (operating system) 90 such as WINDOWS™, a Web browser 92, a motion video playing script 94. A user can access the medical image data providing server 2 via the Web browser 92 to view the medical image data and its related information. In addition, the motion video playing script 94 is a script for playing a plurality of the medical image data in the medical image data providing server 2 as a motion video on a client side, and written in a language such as Java™.

3. Processing when Uploading a Medical Image Data

Figure 7:
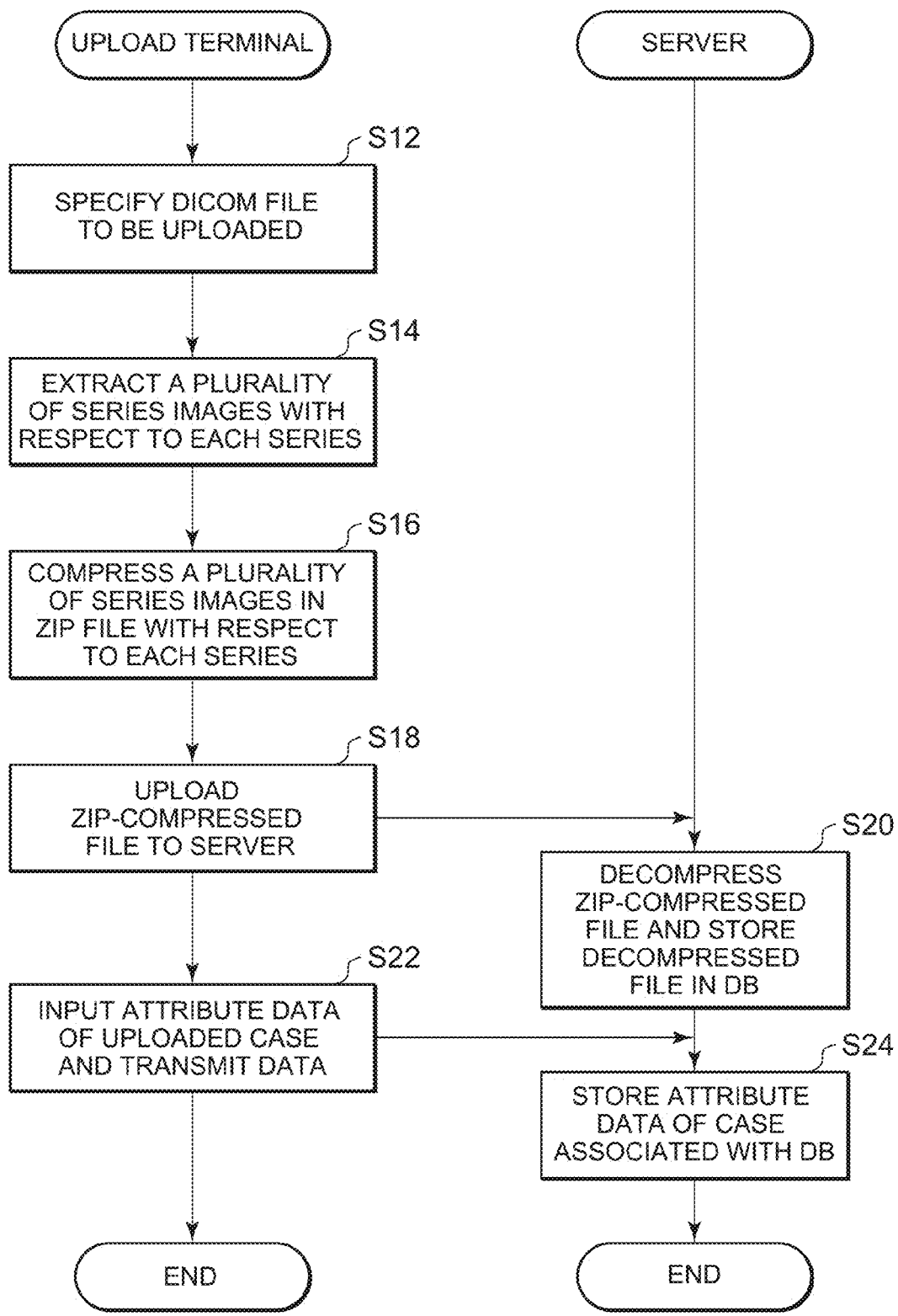
FIG. 7 is a flowchart illustrating a processing when uploading.

Next, a description for processing when uploading medical image data from the upload terminal 6 to the medical image data providing server 2 is provided by using a flowchart shown in the FIG. 7. A processing after login is shown in the flowchart shown in the FIG. 7.

A user who wishes to upload medical image data activates first the uploader 72. In an access screen (FIG. 6) displayed when the uploader 72 is activated, when the user inputs a predetermined user ID and a password, a login is completed through authentication of the medical image data providing server 2.

After login, the user specifies a DICOM file to be uploaded through the keyboard/mouse 68 (step S12 in the FIG. 7). Thus, a plurality of images (for example, in JPEG format) are extracted (step S14), and compressed in a zip file with respect to each series (step S16). Though the DICOM file is compressed into a zip file here, it may be compressed in other formats.

Next, the compressed file is transmitted to the medical image data providing server 2, and then the motion video image is upload-processed (step S18). For example, when a DICOM file including five series of motion video images is selected, five compressed motion video files are uploaded to the medical image data providing server 2.

The medical image data providing server 2 stores whole received series associated with one case ID in the case DB 54 shown in the FIG. 3 (step S20). For example, "a3ef10" (FIG. 3) is granted as a case ID.

At this time, the medical image data providing server 2 stores each frame of the motion video file with a given name as a still image. For example, in the FIG. 3A, extracted still images are each given a file name such as "a3ef10_5_001.jpg, a3ef10_5_002.jpg, a3ef10_5_003.jpg . . . ". "a3ef10" is a case ID, "5" is an ID representing that the fifth motion video in the case ID, and "001, 002, 003 . . . " are frame numbers. Accordingly, each frame of the motion video is stored as a still image in a format in which the frame number is included in the file name.

Thus, a DICOM file having a large file size is compressed and transformed into a format such as JPEG to reduce its file size while being kept in a state with personal information deleted.

Furthermore, in a registration screen as shown in the FIG. 8, attribute information of the uploaded case and the like is separately input and a registration button B1 is pressed by the user, and then the data is transmitted to the medical image data providing server 2 (step S22). Data, such as the name of an operator (Operator) and the age of a patient (Age) as the attribute information is input in a pull-down or free description manner and transmitted to the server 2.

The medical image data providing server 2 stores the attribute information received from the upload terminal 6 associated with each case (for example, case ID "a3ef10") in the case DB 54 (step S24). Uploading the case is thus completed. The DICOM file also includes such attribute information to be input at this step, however, the user inputs the attribute information without extracting the attribute information including patient information from the DICOM data in this embodiment. This is because the attribute information and the like are registered at a level impossible to identify an individual.

4. Processing when Viewing Medical Image Data

A description of processing when viewing an uploaded medical image data is provided below using a flowchart shown in the FIG. 9 and a display example of a viewing screen shown in the FIGS. 10A and B, etc.

Figure 10A:
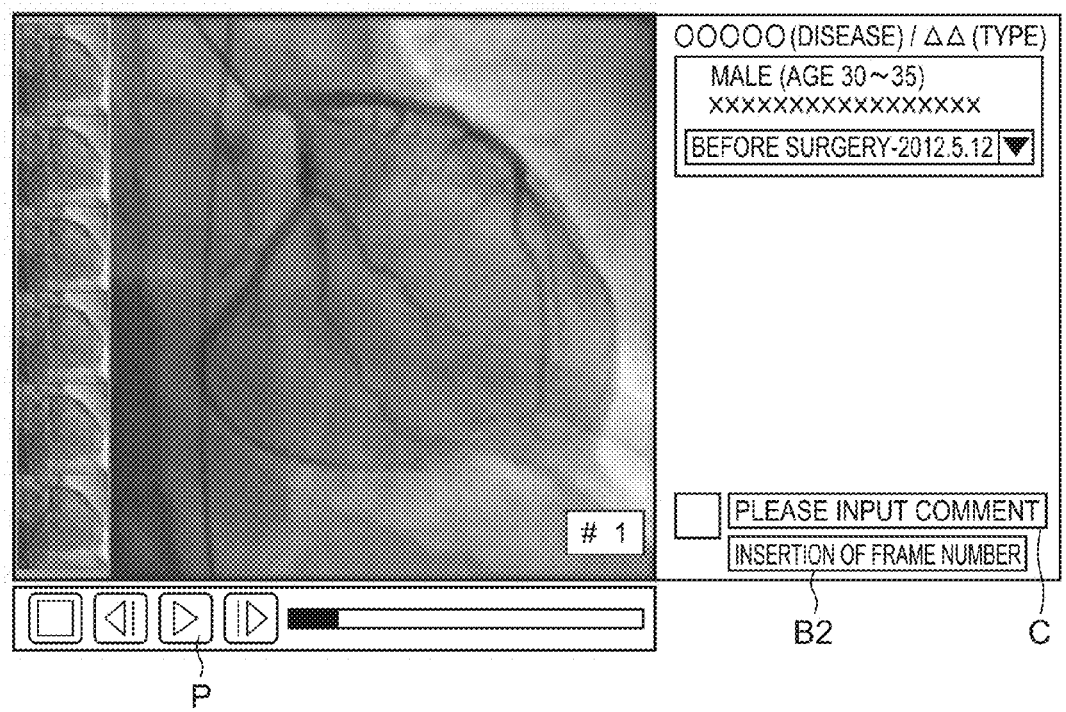
FIGS. 10A and 10B are diagrams illustrating a display example of medical image data.

A user activates the Web browser 92 (FIG. 5) of the viewing terminal 8 and logins to the medical image data providing server 2, and then a viewing screen of a medical image data information as shown in the FIG. 10A is first displayed. In the display shown in the FIG. 10A, a comment column on the right side of the medical image display is blank. In addition, in the FIGS. 10A and 10B, a thumbnail of the medical image data (image cited in the comment) having high importance is displayed on the left side of a main image area M.

A user specifies a case and presses a play button P, and then a series of still images corresponding to the case are transmitted from the medical image data providing server 2. The still images are played by the viewing terminal 8 in the order of frames number included in file names of the still images being transmitted. The motion video is thus displayed. A program for playing the still images in the order of the frame numbers included in the file names is provided from the medical image data providing server 2 as JAVASCRIPT, as described above.

A description is provided below of a case where a user plays and views the motion video image, and pauses viewing at a position of frame ID "#131" to input a comment on an observation. Once the play button P is pressed, this button will be a pause button.

When a user presses an insertion button B2 below a comment input field C displayed in the lower right portion of the viewing screen at a position of the ID "#131" (step S32 of the FIG. 9), a link destination information for accessing the currently displayed medical image ID "#131" (here, a repository URL of the still image recorded in the server) is first inserted in the comment input field C as "#131" by a hyperlink (step S34). For example, a URL showing an address on the server 2 storing the medical image data corresponding to "[a3ef10]_[1]_[131] shown in the FIG. 3A" is displayed in the comment input field C as "#131" by a hyperlink. The link destination information may be inserted before inputting a comment or when inputting the comment. In addition, link destination information to be inserted may be medical image data in a series of different motion video images, or may be medical image data of a different case.

The user further inputs a comment such as observation through the keyboard/mouse 88 (FIG. 5), and presses an ENTER key (step S36). The input comment is thus associated with the ID of the user who input it as shown in the FIG. 11 and then, stored (accumulated) in the case DB 54 in chronological order (step S38). Accordingly, a comment "I made a judgment that ×× by ○○. It is around "#131"." as shown in the FIG. 10B is displayed on a screen (step S40).

Figure 12:
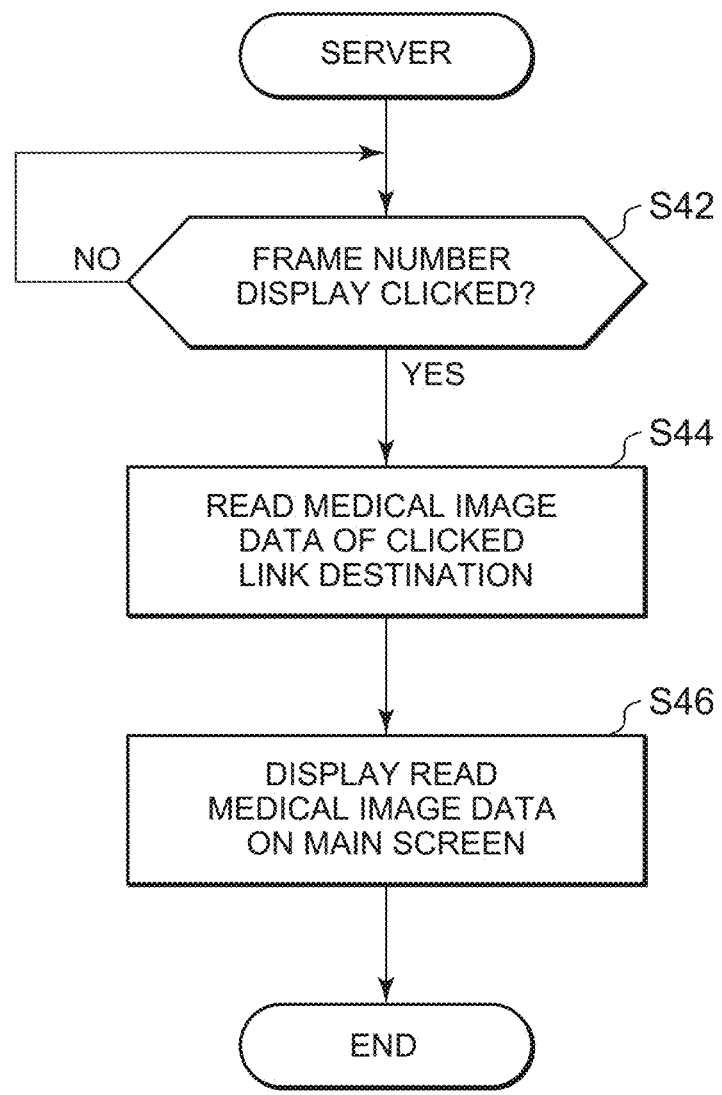
FIG. 12 is a flowchart illustrating processing when a frame number is clicked.
Figure 13:
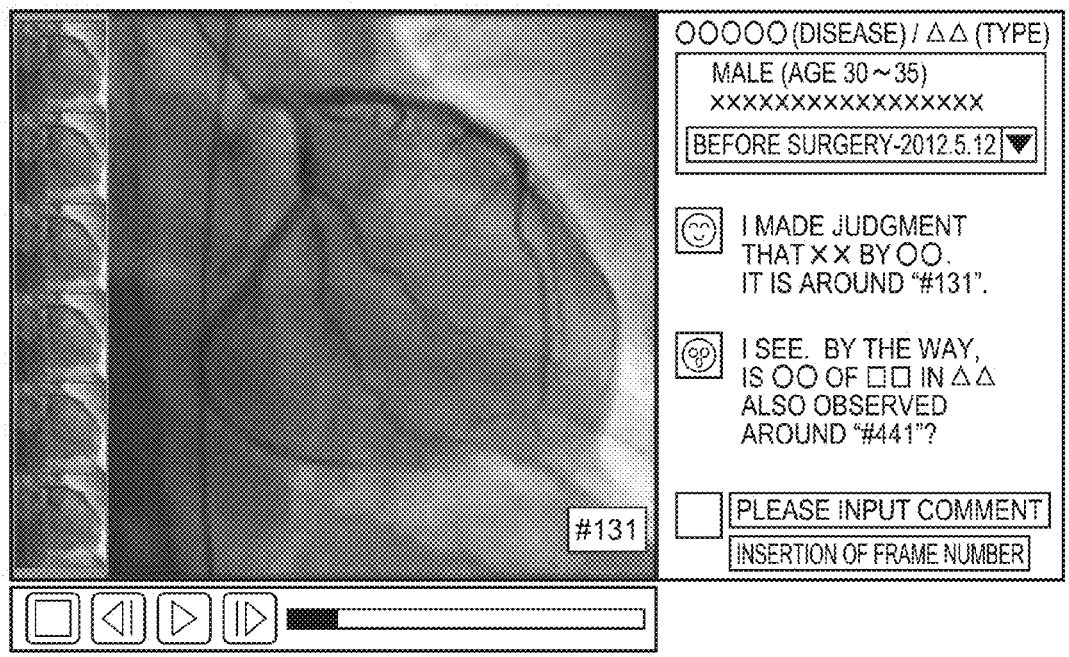
FIG. 13 is a diagram illustrating a display example of medical image data.

Next, a medical image data information display program 56 recognizes that a user (for example, a user different from the above user) clicks a link part (for example) in the comment when viewing the motion video ("Yes" of step S42 in the FIG. 12), and then medical image data of the link destination is read out from the case DB 43 (step S44) and displayed on the main image area M as shown in the FIG. 13 (step S46).

Figure 10B:
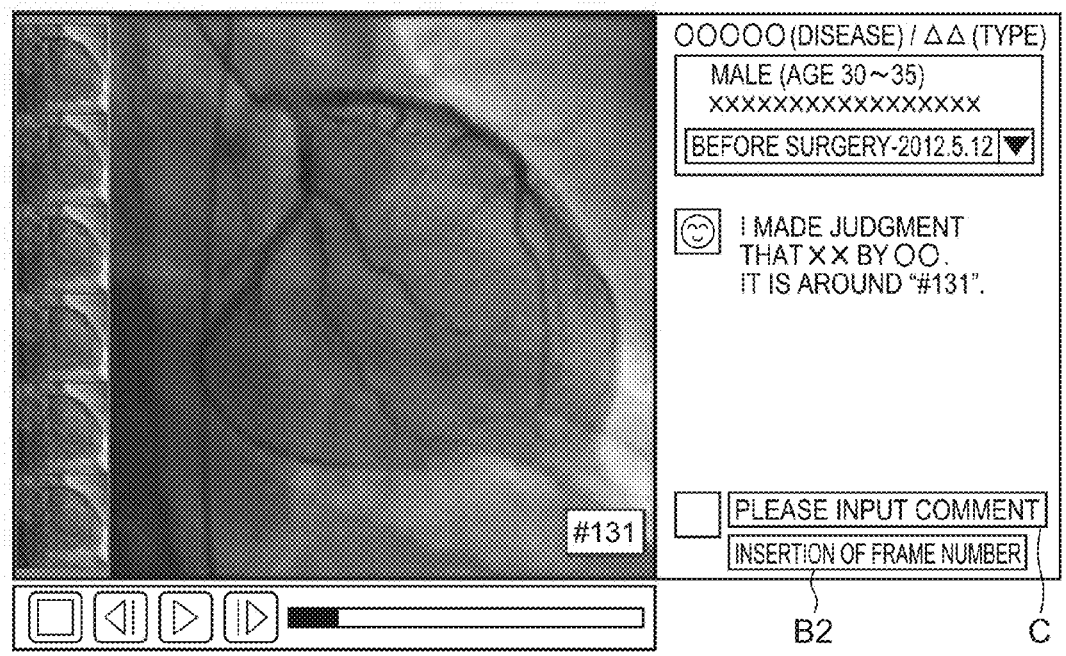

A screen display shown in the FIG. 13 shows a state after the link part "#131" included in the past comment is further clicked by a user who commented on the frame "#441" from the state shown in the FIG. 10B. The read out medical image data may also be displayed on a subscreen adjacent to the main image area M or displayed in an additional window by mouseover (pop-up display) instead of displaying the read out medical image data on the main image area M.

As described above, a comment of a user (medical personnel who interprets the image) on the case is accumulated and displayed on a screen in chronological order together with a link destination information (FIG. 13), and thereby an easy access to cited medical image data on a past comment can be achieved.

Figure 14:
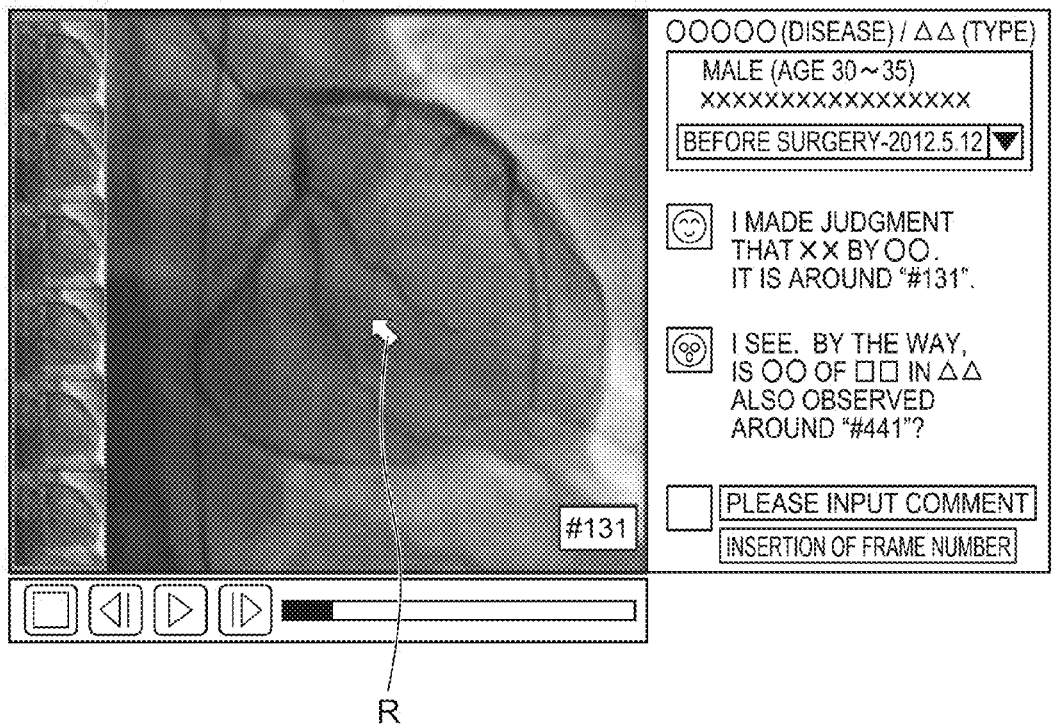
FIG. 14 is a diagram illustrating a display example of medical image data.

Furthermore, a mark as an identification label (such as an arrow) may be incorporated into the display area of the medical image (that is the medical image data) at the time of, for example, inputting the comment, by putting an arrow mark R in the medical image through the keyboard/mouse 88 as shown in the FIG. 14.

Figure 9:
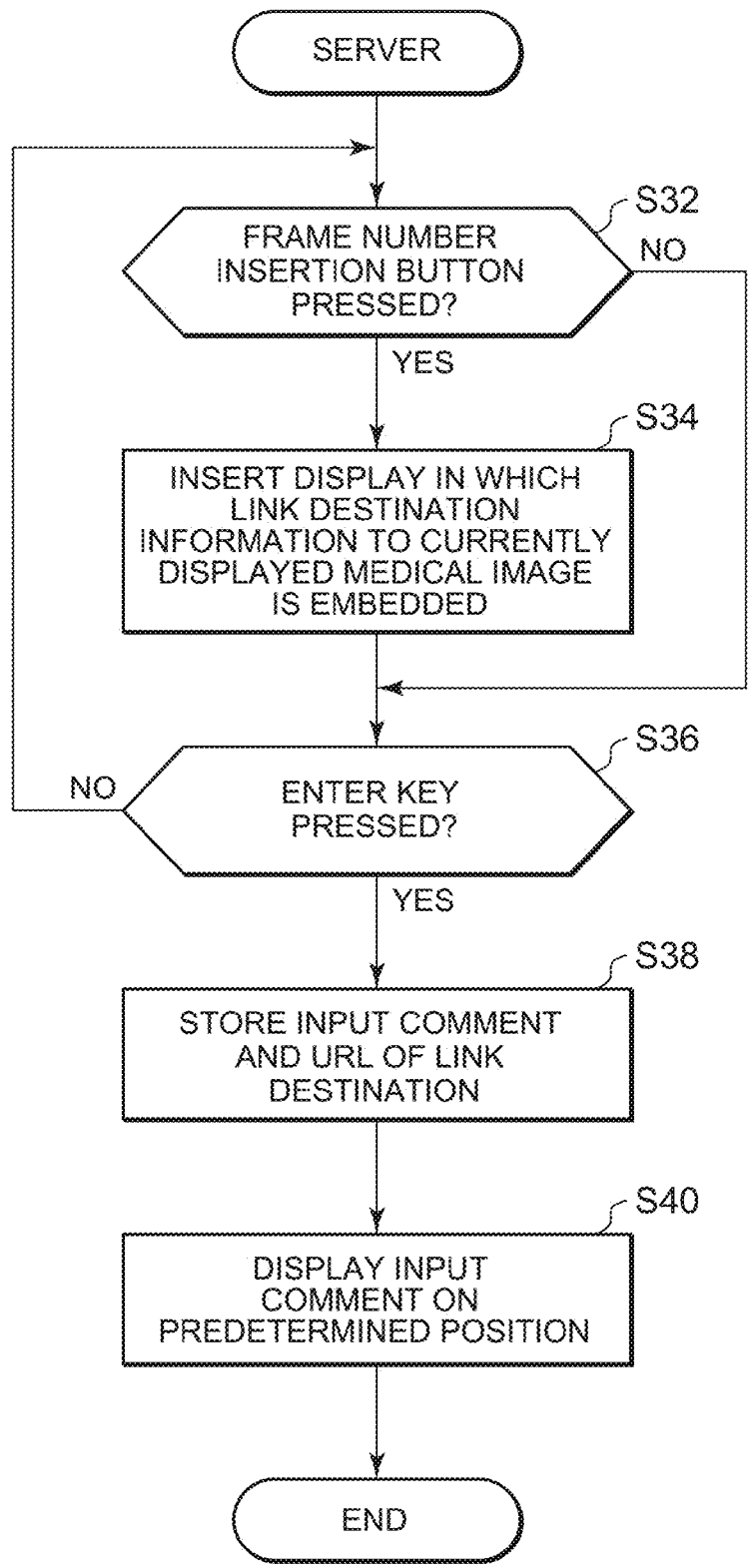
FIG. 9 is a flowchart illustrating a processing when inserting a frame number in a comment.
Figure 15:
FIG. 15 is a diagram illustrating a data example of a mark incorporated in a medical image data.

For example, when the comment input in the step S38 in the FIG. 9 is stored, coordinate information about the arrow mark R put in the medical image associated with each frame may be stored in an additional table (FIG. 15). In an example shown in the FIG. 15, when the motion video image is viewed, a display frame is determined to be displayed serially before and after the frame such that the arrow mark R is displayed just for predetermined time (for example, for a few seconds). Thus, the arrow mark R put in a predetermined frame can be displayed at the next time of playing.

In the above, arrow mark R is incorporated into the specific frame of the medical image data, however, other ways, for example, enclosing a specific area by a line or otherwise displaying using a luminance difference without enclosing by a line may be used. In addition, an attribute (such as name, affiliation, specialism, and age) of the user who input the comment may be displayed in conjunction with the identification labeling.

Figure 16:
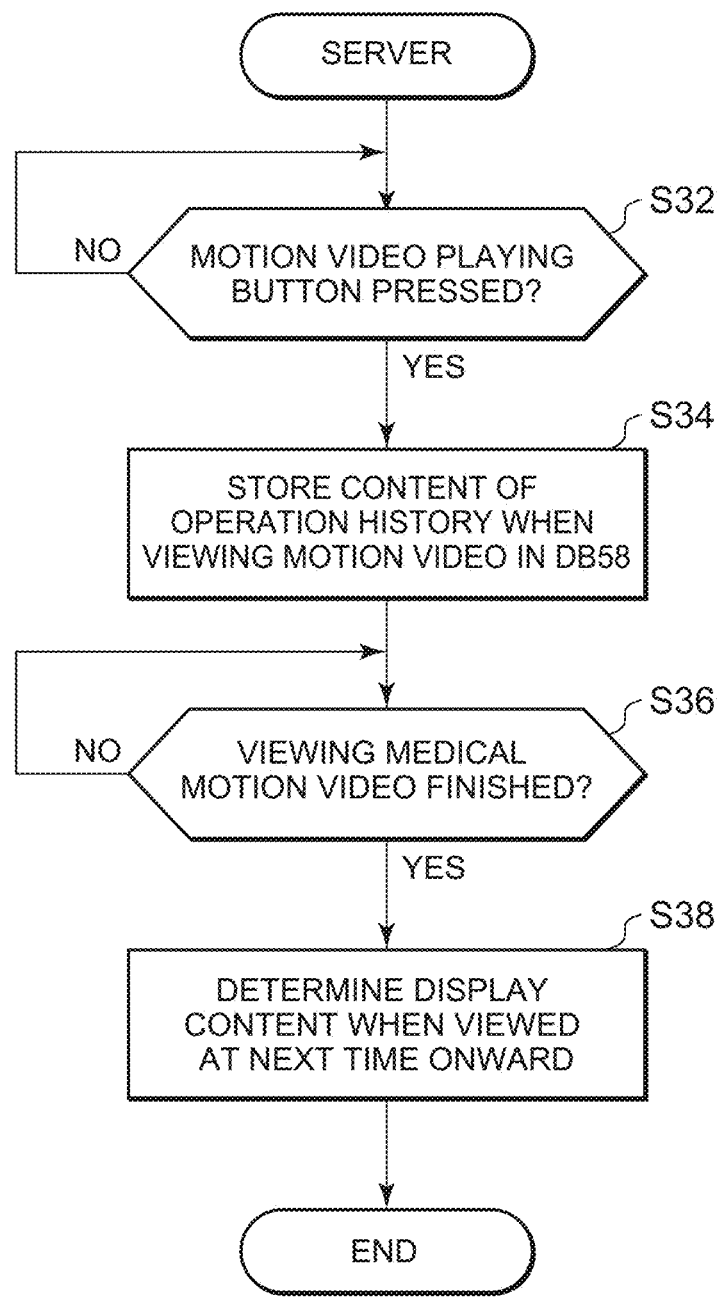
FIG. 16 is a flowchart illustrating a processing from accumulation of an operation history to determination of display content when viewed from the next time onward.

5. Processing when Operation Histories are Accumulated and the Medical Image is Viewed from the Next Time Onward FIG. 16 is a flowchart illustrating processing performed by the medical image data information display program 56 when a medical motion video is played.

When playing of the medical motion video is started ("Yes" of step 52 shown in the FIG. 16), the CPU 20 of the medical image data providing server 2 starts accumulating operation histories received from the viewing terminal 8 (step S54).

That is, the CPU 20 of the medical image data providing server 2 stores a user's operation history (such as a content of an operation and the number of operations) when viewing the motion video in the operation history DB 58. A content of the operation includes, for example, a pause operation, fast-forward operation, rewind operation, frame advance operation, frame return (reverse frame advance) operation and the like.

Figure 17:
FIG. 17 is a diagram illustrating a data example of content of an operation when viewing.
Figure 18:
FIG. 18 is a diagram illustrating a data example of display frequency with respect to each frame.

In the FIGS. 17 and 18, data examples of an operation kind table and a display frequency table included in the operation history DB 58 of the medical image data providing server 2 are shown, respectively.

In the operation type table shown in the FIG. 17, content of an operation of each user associated with a frame ID when the operation is performed is stored in chronological order. In the display frequency table shown in the FIG. 18, the display frequency indicating a display frequency of the frame is stored with respect to each frame.

Figure 19A:
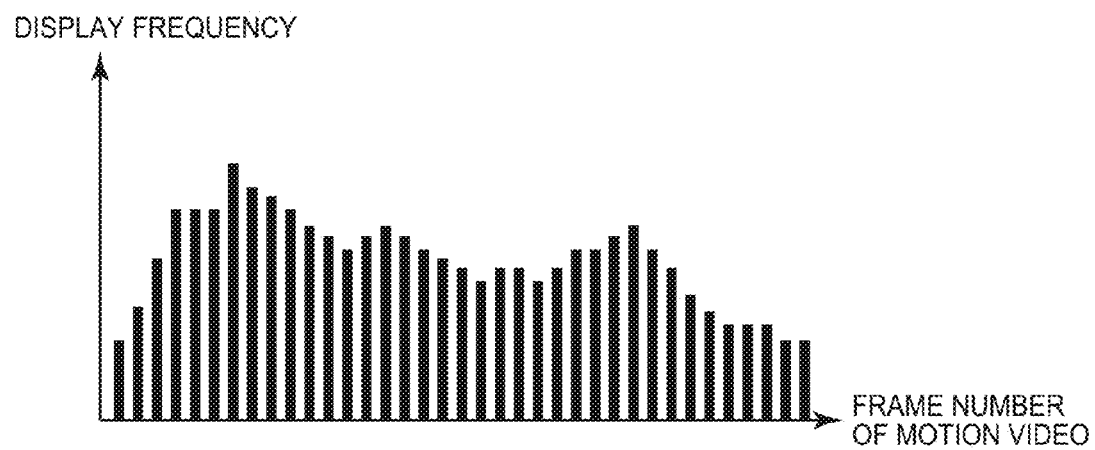
FIGS. 19A and 19B are diagrams illustrating a content of an operation and a display frequency graphically.
Figure 19B:
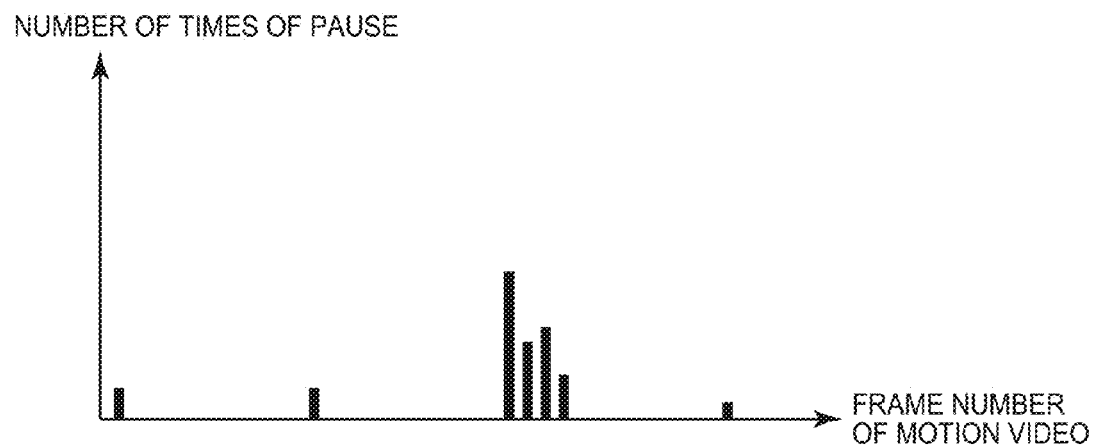

In the FIG. 19A, an example of a graphed display frequency (histogram display) based on data in the display frequency table shown in the FIG. 18 with respect to each frame is shown. In the FIG. 19B, an example of a graphed pause frequency (histogram display) with respect to each frame, when viewing based on the operation kind table shown in the FIG. 17, is shown.

When the CPU 20 of the medical image data providing server 2 recognizes that a viewing of medical motion video is finished (for example, a stop button is pressed) ("Yes" of step S56), the CPU 20 determines a content of a display from the next time of viewing based on the content of the operation history described above (step S58).

Figure 20:
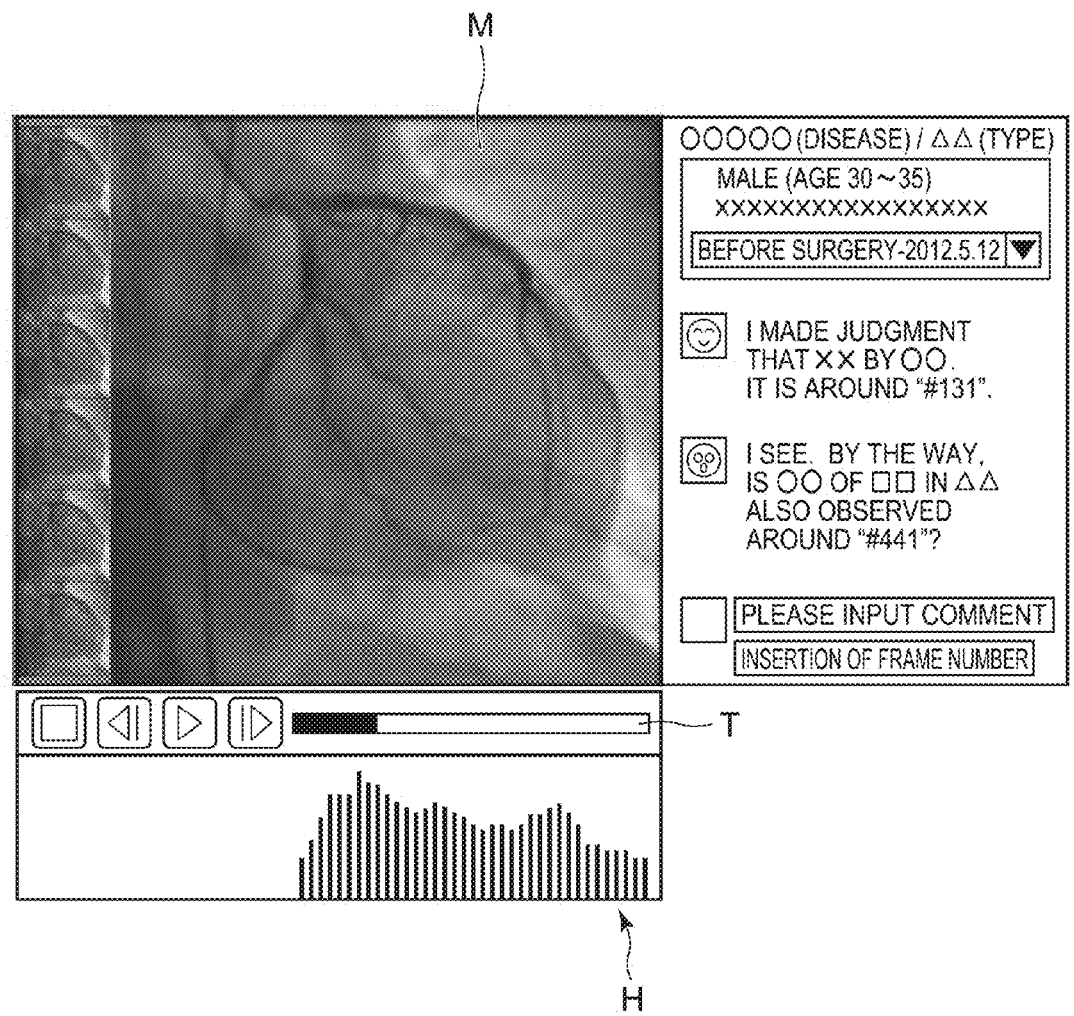
FIG. 20 is a diagram illustrating a display example of a medical image data.

For example, as shown in the FIG. 20, it is determined that the display frequency of a frame H is displayed as a histogram (FIG. 19A) in chronological order below the main image area M along a time bar T. Thus, a user (the user of the viewing terminal 8*b* shown in the FIG. 1) who views a motion video from the next time onward can select a position corresponding to a part having high interpretation frequency in the past (peak of the histogram) to play and view.

Another display method, such as displaying the pause frequency when viewing alone or together with the display frequency of the frame H shown in the FIG. 20 as a histogram (FIG. 19B) below the main image area M along the time bar T in chronological order with respect to each frame may be determined.

Figure 21:
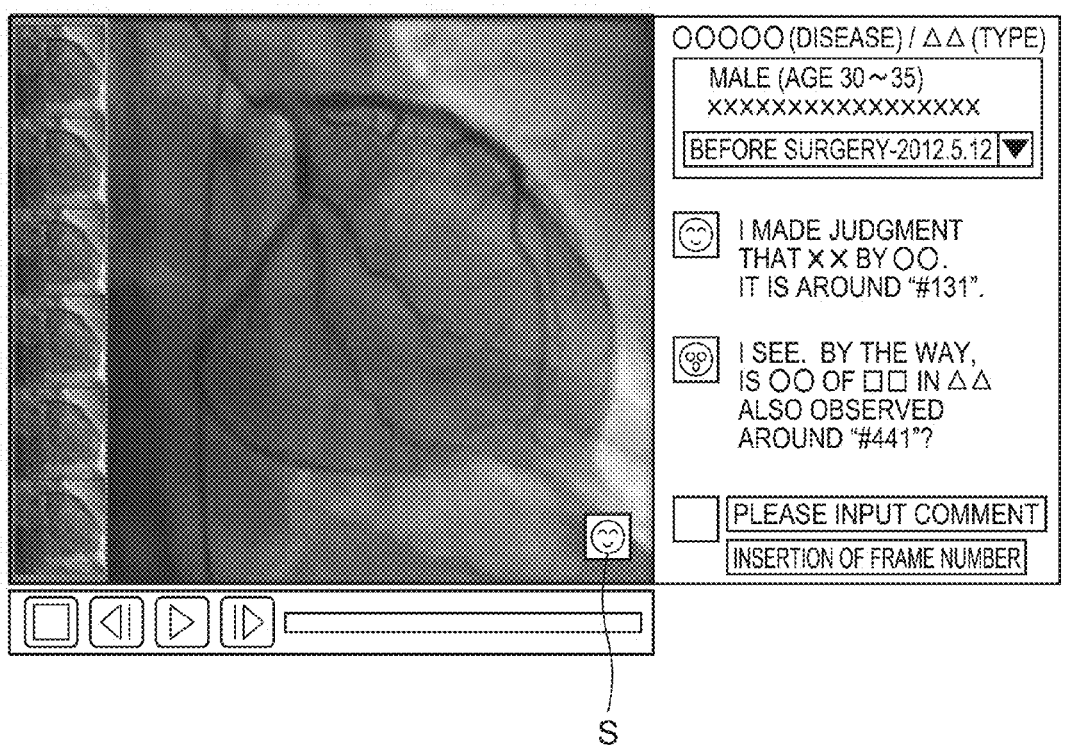
FIG. 21 is a diagram illustrating a display example of a medical image data.

In addition, as shown in the FIG. 21, with respect to a frame having a high frequency of viewing by a specific user, an identification mark S of the user may be displayed in a specific frame.

The basis for determination of identification labeling may be, without being limited to display frequency, a total display time of each frame or a point calculated by, for example, adding 2 points to the frame advance operation. In addition, summing operation history data for all users or limiting to only an operation history data of the specified user may be selected.

Thus, a display method from the next time onward is determined while operation history data are accumulated in the database every time the user plays the motion video, and thereby, observations can be accumulated among medical personnel to exchange information smoothly.

Other than the display method exemplified above, a display method in which the motion video is paused or played in slow motion at a position (frame) having high importance when play may be selected for the display method when viewed from the next time onward.

Furthermore, in the FIG. 10 etc., a thumbnail of medical image data (an image cited in a comment) having high importance is displayed on the left side of the main image area M, however the medical image data having high importance may be given color, given a mark, or given different colors in a descending order of importance.

6. Other Embodiments

In the above embodiment, medical motion video data is played in sequence by converting each frame of the medical motion video data into a still image data in JPEG format etc. and assigning file names to each still image data in the order of frame numbers. An effect that the medical motion video is played easily and also a link to each still image is made easily is thus provided.

However, while there is an advantage in the method as described in the above embodiment, there is the problem that a special playing program for playing a motion video (for example, motion video playing script 94 in the FIG. 3) is needed.

To solve this problem, an uncompressed motion video data may be recorded in the medical image data providing server 2, and the frame number of the uncompressed motion video data may be specified and linked. In this instance, unlike the previous embodiment, the motion video data is recorded as a single file. In addition, since a frame number originally provided to the motion video data is used, there is no need to provide a separate ID and the like.

Furthermore, motion video data as MPEG data etc. may be recorded in the medical image data providing server 2. In this instance, it is not possible to link to each frame directly. Thus, linking is achieved as follows.

A user clicks a reference button in the viewing terminal 8 shown in the FIG. 1, and then a frame number of an image being displayed at that time is created as link information and transmitted to the medical image data providing server 2. The medical image data providing server 2 records this frame number as link information together with a comment and the like.

The link is clicked in the viewing terminal 8 at the time of referring, and then the frame number of the image is transmitted to the medical image data providing server 2. In the medical image data providing server 2, based on this frame number, it is determined in which packet of the MPEG motion video data the frame number is included. This determination is made by referring the range of the frame numbers recorded in the packet. The packet is thus specified, and then, images of a plurality of frames are created from the packet, and an image of specified frame number is extracted to be transmitted to viewing terminal 8.

The motion video image data is extracted from DICOM file in the above embodiment, however, without being limited to the DICOM file, the motion video image data may be extracted from other original standard data.

Figure 22:
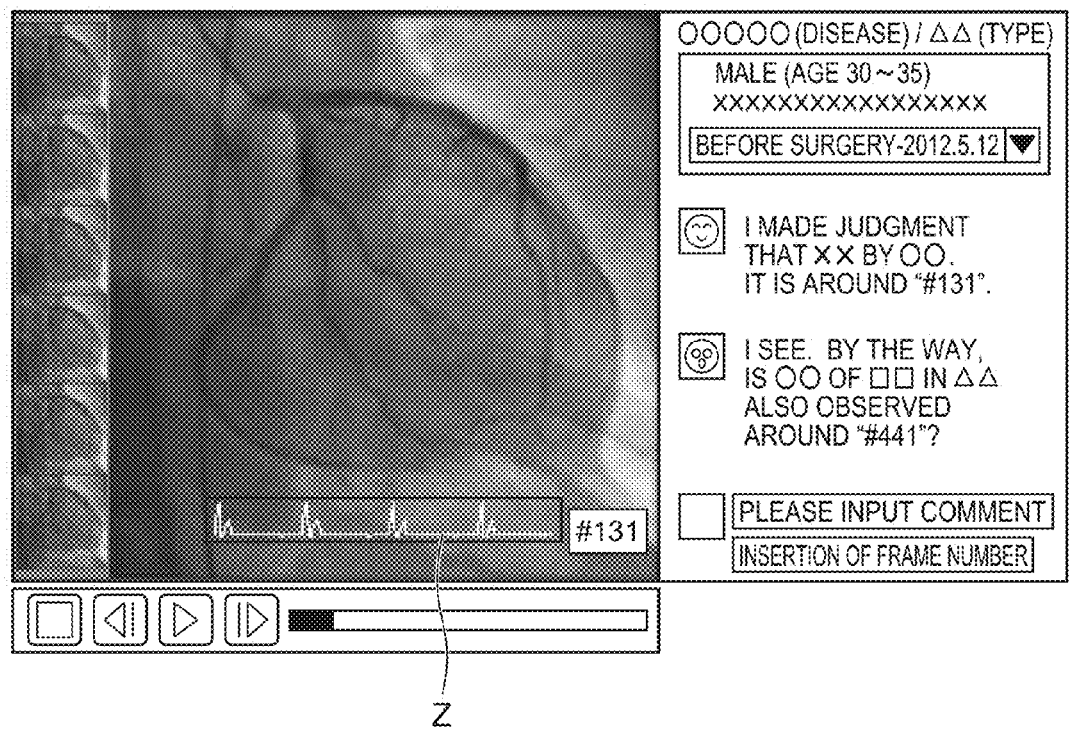
FIG. 22 is another diagram illustrating a display example of a medical image data.

Only a medical image is displayed on the main image area M in the above embodiment, however, as shown in the FIG. 22, another image Z such as heart rate may also be displayed over the main image area M.

A comment is stored with respect to a case in the above embodiment, however, the comment may be stored with respect to each frame.

The medical image data providing system server 2 is a PC in the above embodiment, however, other devices (such as workstations) may also be used.

The upload terminal 6 and the viewing terminal 8 are PCs in the above embodiment, however, other devices (such as smartphones and tablet terminals) may also be used.

A plurality of images constituting a motion video are extracted from the DICOM file in the above embodiment, however, a series of still images (such as sectional images of CT taken from head to foot) may also be extracted.

The uploader 72 of the upload terminal 6 is used to upload a motion video image in the above embodiment, however, without being limited to this, other means such as Web browser may also be used to upload the motion video image.

The Web browser 92 of the viewing terminal 8 is used to view a medical image data in the above embodiment, however, the medical image data may also be displayed by providing a dedicated application for viewing in the viewing terminal 8 and using this application.

A plurality of sets of motion video images are included in a DICOM file (one case) in the above embodiment, however, the number of the motion video image included in the DICOM file (one case) may be one.

A motion video image extracted from a DICOM file on the upload terminal 6 side is transmitted to the medical image data providing server 2 in the above embodiment, however, the DICOM file may be transmitted to the medical image data providing server 2 as it is, and then extracted in the medical image data providing server 2.

Medical image data (frame) of the same case are cited in the above embodiment, however, medical image data (frame) of other case may also be cited.

In the above embodiment, as illustrated in the FIG. 3A, a frame number is used as a file name of a still image corresponding to each frame of a motion video to create a link to the file name. However, as illustrated in the FIG. 3B, each still image file may be provided with a corresponding ID and be stored as a table. In this instance, the ID is inserted as a parameter of the link from a viewing terminal, and the medical image data providing server 2 that received the ID acquires the corresponding still image based on the ID and transmits to the viewing terminal.

What is claimed is:

1. A server device comprising:
   a recording part that records each frame of motion video image data as a still image and a consecutive number of playing order as a motion video as a file name or an index name of each of the still images and records a comment input from a terminal device;
   first transmission means that receives a playing instruction from the terminal device and transmits the still images; and
   second transmission means that receives a link destination acquisition instruction from the terminal device and acquires the still image corresponding to the consecutive number described in the file name or the index name included in the link destination acquisition instruction, and then transmits the still image.

2. The server device according to claim 1, wherein the server device comprises:
   means for storing a user's operation history of the terminal device when playing the motion video; and,
   means for determining a display method of playing the motion video from the next time onward based on the user's operation history.

3. The server device according to claim 2, wherein the operation history is the number of pause operation stored with respect to each frame of the image data.

4. The server device according to claim 2, wherein the operation history is a display frequency with respect to each frame.

5. The server device according to claim 1, wherein the first transmission means of the server device transmits information of a frame to be thumbnailed with the comment and the motion video data, and the frame to be thumbnailed is determined based on the operation history.

6. A non-transitory computer readable information storage media having stored thereon instructions that when executed by a computer cause to be performed a method comprising:
   recording each frame of motion video image data as a still image and a consecutive number of a playing order as a motion video as a file name or an index name of each of the still images;
   recording a comment input from a terminal device, wherein the computer is controlled by the instructions to so as to function as:
   a first transmission means that receives a playing instruction from the terminal device and transmits the still images; and,
   a second transmission means that receives a link destination acquisition instruction from the terminal device, and acquires the still image corresponding to the consecutive number described in the file name or the index name included in the link destination acquisition instruction and then transmits the still image.

7. The media according to claim 6,
   wherein the computer is controlled by the instructions so as to function as:
   a means for storing a user's operation history of the terminal device when playing the motion video; and a means for determining a display method of playing the motion video from the next time onward based on the user's operation history.

8. The media according to claim 7, wherein the operation history is the number of pause operation stored with respect to each frame of the image data.

9. The media according to claim 7, wherein the operation history is a display frequency with respect to each frame.

10. The media according to claim 6, wherein the first transmission means of the server device transmits information of a frame to be thumbnailed with the comment and the motion video data, and the frame to be thumbnailed is determined based on the operation history.

11. A terminal device comprising:
first display control means that displays a series of still images transmitted from a server device in response to a playing instruction as a motion video by playing in consecutive numerical order described in a file name or an index name and also displays a comment;
link destination acquisition instruction transmission means that transmits the link destination acquisition instruction with the consecutive number to the server device when a link displayed in the comment is selected based on link information including the consecutive number; and
second display control means that displays the still images transmitted from the server device in response to the link destination acquisition instruction.

12. The terminal device according to claim 11, wherein the terminal device comprises link information insertion means which, when a link operation is made by a user when displaying the motion video by the first display control means, creates the link information specifying the frame number of displayed motion video and inserts it in the comment.

13. The terminal device according to claim 11, wherein the terminal device comprises link information insertion means which, when a link operation is made by a user when displaying the motion video by the first display control means, creates the link information specifying the consecutive number of displayed motion video and inserts it in the comment.

14. A non-transitory computer readable information storage media having stored thereon instructions that when executed by a computer cause to be performed a method comprising:
displaying, by a first display control means, a series of still images transmitted from a server device in response to a playing instruction as a motion video by playing in consecutive numerical order described in a file name or an index name and also displays a comment;
transmitting, by a link destination acquisition instruction transmission means, the link destination acquisition instruction with the consecutive number to the server device when a link displayed in the comment is selected based on link information including the consecutive number; and
displaying, a by second display control means, the still images transmitted from the server device in response to the link destination acquisition instruction.

15. The media according to claim 14, further comprising: when a link operation is made by a user when displaying the motion video by the first display control means, creating, by a link information insertion means, the link information specifying the frame number of displayed motion video and inserts it in the comment.

16. The media according to claim 14, further comprising: when a link operation is made by a user when displaying the motion video by the first display control means, creating, by a link information insertion means, the link information specifying the consecutive number of displayed motion video and inserts it in the comment.

* * * * *